(12) United States Patent
Ellenbogen (10) Patent No.: US 7,224,765 B2
(45) Date of Patent: *May 29, 2007

(54) COMPUTED TOMOGRAPHY SYSTEM (75) Inventor: Michael P. Ellenbogen, Wayland, MA (US)

(73) Assignee: Reveal Imaging Technologies, Inc., Bedford, MA (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/971,453

(22) Filed: Oct. 21, 2004
(Under 37 CFR 1.47)

(65) Prior Publication Data
US 2005/0169422 A1 Aug. 4, 2005

Related U.S. Application Data (63) Continuation-in-part of application No. 10/677,976, filed on Oct. 2, 2003.

(51) Int. Cl.
*G01N 23/00* (2006.01)

(52) U.S. Cl. .......................................... 378/19; 378/57

(58) Field of Classification Search .................... 378/4, 378/19, 57
See application file for complete search history.

(56) References Cited

U.S. PATENT DOCUMENTS

| | | | |
|---|---|---|---|
| 4,029,963 A | 6/1977 | Alvarez et al. | |
| 4,070,581 A | 1/1978 | Gibbons et al. | |
| 4,075,492 A | 2/1978 | Boyd et al. | |
| 4,138,721 A | 2/1979 | Boyd | |
| 4,149,078 A | 4/1979 | Hahn et al. | |
| 4,149,079 A | 4/1979 | Ben-Zeev et al. | |
| 4,247,774 A | 1/1981 | Brooks | |
| 4,266,136 A | 5/1981 | Duinker | |
| 4,298,799 A | 11/1981 | Oliver | |
| 4,315,157 A | 2/1982 | Barnes | |

(Continued)

FOREIGN PATENT DOCUMENTS

EP    0 471 455 A2    2/1992

(Continued)

OTHER PUBLICATIONS

U.S. Appl. No. 10/971,453, filed Oct. 21, 2001, Ellenbogen.

(Continued)

*Primary Examiner*—Courtney Thomas
(74) *Attorney, Agent, or Firm*—Mintz, Levin, Cohn, Ferris, Glovsky and Popeo, P.C.

(57) ABSTRACT

An embodiment of the invention is directed to a computed tomography device, comprising a tunnel to receive baggage, an x-ray source providing an x-ray beam that intersects the tunnel and has a beam angle of 120°, a gantry that oscillates relative to the tunnel through an oscillation angle that equals 270°, and a plurality of detectors. The plurality of detectors are mounted to the gantry and adapted to receive x-rays from the x-ray source. In addition, the plurality of detectors are arranged in a horseshoe-shaped configuration in which at least one first detector is located a furthest distance from the x-ray source and at least one second detector is disposed on each side of the at least one first detector and is disposed closer to the x-ray source than the at least one first detector.

88 Claims, 5 Drawing Sheets

U.S. PATENT DOCUMENTS

| | | | |
|---|---|---|---|
| 4,599,740 A | 7/1986 | Cable | |
| 4,756,015 A | 7/1988 | Doenges et al. | |
| 4,759,047 A | 7/1988 | Donges et al. | |
| 4,783,794 A | 11/1988 | Dietrich | |
| 4,796,183 A | 1/1989 | Ermert et al. | |
| 4,798,183 A | 1/1989 | Hataura et al. | |
| 4,817,121 A | 3/1989 | Shimizu et al. | |
| 4,841,554 A | 6/1989 | Doenges et al. | |
| 4,870,670 A | 9/1989 | Geus | |
| 5,164,973 A | 11/1992 | Takahashi et al. | |
| 5,367,552 A | 11/1994 | Peschmann | |
| 5,570,403 A | 10/1996 | Yamazaki et al. | |
| 5,583,903 A | 12/1996 | Saito et al. | |
| 5,661,774 A | 8/1997 | Gordon et al. | |
| 5,692,029 A | 11/1997 | Husseiny et al. | |
| 5,848,117 A | 12/1998 | Urchuk et al. | |
| 5,867,553 A | 2/1999 | Gordon et al. | |
| 5,912,938 A | 6/1999 | Dobbs et al. | |
| 5,917,876 A | 6/1999 | Fujii et al. | |
| 6,018,562 A | 1/2000 | Willson | |
| 6,185,272 B1 | 2/2001 | Hiraoglu et al. | |
| 6,218,943 B1 | 4/2001 | Ellenbogen | |
| 6,301,326 B2 * | 10/2001 | Bjorkholm | 378/57 |
| 6,335,957 B1 | 1/2002 | DiBianca | |
| 6,647,091 B2 | 11/2003 | Fenkart et al. | |
| 6,658,082 B2 | 12/2003 | Okumura et al. | |
| 6,707,879 B2 | 3/2004 | McClelland et al. | |
| 2004/0120454 A1 | 6/2004 | Ellenbogen et al. | |

FOREIGN PATENT DOCUMENTS

| | | |
|---|---|---|
| EP | 0 816 873 A1 | 1/1998 |
| EP | 0 825 457 A1 | 2/1998 |
| WO | WO 96/13839 | 5/1996 |
| WO | WO 97/18462 | 5/1997 |
| WO | WO 03/029844 A2 | 4/2003 |
| WO | WO 03/065077 A2 | 8/2003 |
| WO | WO 2004031755 A2 | 4/2004 |
| WO | WO 2004031755 A3 | 4/2004 |

OTHER PUBLICATIONS

Defandants' Objections and Answers to Plaintiff's Second Set of Interrogatories, dated May 31, 2005, in a case entitled *L-3 Communications Security and Detection Systems Corporation Delaware v. Reveal Imaging Technologies, Inc.*, Michael Ellenbogen, Richard Bijjani, James Buckley, Bruce Lee, John Sanders and Elan Scheinman, Commonwealth of Massachusetts, Superior Court Department (BLS) of the Trial Court, Civil No. 03-05810 BLSI (Justice van Gestel).

Plaintiff's Second Set of Interrogatories to Defendants, dated Apr. 13, 2005, in a case entitled *L-3 Communications Security and Detection Systems Corporation Delaware v. Reveal Imaging Technologies, Inc.*, et al., Commonwealth of Massachusetts, Superior Court Department (BLS) of the Trial Court, Civil No. 03-05810 BLSI (Justice van Gestel).

Nick Fox, "X-ray Screening Uncovered" Airport Safety Security Service, vol. 5, Oct. 2004.

InVision Technologies, "Technical Specifications" for CTX9000 DSI.

L-3 Communications, literature ofr eXaminer 3DX6000, http://www.dsxray.com/Linescan.asp?ProductCode=eXaminer6, Aug. 2, 2004, pp. 1-3.

Analogic product literature, "The Exact: An Advanced Explosive Detection System,".

Federal Register, "Part IX, Department of Transportation," Federal Aviation Admin., Explosives Detection Systems; Notices, Monday Apr. 13, 1998.

L-3 Communications Security and Detection Systems, Inc., VividCT Series, www/bombdetection.com; Rev. Oct. 2002.

Rapiscan X-ray System Maintenance Manual 1995.

Terry Peters, "CT Image Reconstruction," SLIDES REVL 05697-05745, pp. 1-49.

Michael D. Silver, "High-helical-pitch, cone-beam computed tomography," Phys. Med. Biol., 43 (1998) 847-855, REVL 05688-05696.

Dan Kedem, et al, "Computed Tomography for Thick Steel Pipes and Castings," Electric Power Research Inst., Dec. 1986, REVL 05565-05682.

U.S. Army Medical Research Acquisition Activity, Contract DAMD17-87-C-7108, Dated Jun. 1, 1987; REVL 05479-05487.

Berthold K.P. Horn, "Fan-Beam Reconstruction Methods," A.I. Memo No. 448, Nov. 1977 REVL 05425-05469.

Patrick Michael, et al, "The Architecture of Secure Flow," REVL 05288-05295.

Tim Rayner et al., "Threat Vector Solutions," REVL 05283-05287.

Heimann, Check-In Counter X-Ray Systems CS 5070, REVL 4936-4941.

MUX Training, Apr. '03, with CTX9000 DSI Product Announcement, REVL 4926-4932.

InVision Technologies, "A Clear Vision, A Vital Mission," REVL 4933-4935.

Jim Aldo et al., "Enhanced Integration, Data Fusion and Communication Protocols for Integrated Checked Baggage Explosives Detection Screening," Nov. 1996, pp. 385-390,REVL 4909-4913.

Dr. Wagih Hassan Makky, "Proceedings of the Second, Explosives Detection Technology Symposium & Aviation Security Technology Conference," REVL 4781-4788.

David S. de Moulpied et al., Security Management, Mar. 1992, REVL 4855-4898.

InVision Technologies, "A Clear Vision, A Vital Mission," REVL 4778-4780.

InVision Technologies, Product Announcement, Multiplexing for the CTX 9000 DSi, REVL 4772-4777.

"Proceedings, IEEE Dec. 1979, Collecting Data with Fan Beams," REVL 4759-4769.

KSI Kaiser System Inc., OmniBlock X-Ray Source, REVL 4768-4769.

Invision Technologies, Image Archiving, REVL 4897-4898.

Slide entitled L-Shaped Array (Conventional X-Ray Technology).

The Reveal Parties' Opposition to Plaintiff's Emergency Motion Regarding "Newly Found Evidence" in a case entitled *L-3 Communications Security and Detection Systems Corporation Delaware v. Reveal Imaging Technologies, Inc.*, Commonwealth of Massachusetts, Superior Court Department (BLS) of the Trial Court, Civil No. 03-05810-BLS (Justice van Gestel).

Deposition of David A. Schafer dated Thursday, May 12, 2005, in a case entitled *L-3 Communications Security and Detection Systems Corporation Delaware v. Reveal Imaging Technologies, Inc.*, Commonwealth of Massachusetts, Superior Court Department (BLS) of the Trial Court, Civil No. 03-05810-BLS (Justice van Gestel). including exhibits 1,6,7, 10-19.

Documents bearing production numbers REVL 05746 to REVL 05761 produced by the defendant in a case entitled *L-3 Communications Security and Detection Systems Corporation Delaware v. Reveal Imaging Technologies, Inc.*, Commonwealth of Massachusetts, Superior Court Department (BLS) of the Trial Court, Civil No. 03-05810-BLS (Justice van Gestel).

Affidavit of James Buckley in Opposition to Plaintiff's Patent Motions, Redacted Version, in a case entitled *L-3 Communications Security and Detection Systems Corporation Delaware v. Reveal Imaging Technologies, Inc.*, Commonwealth of Massachusetts, Superior Court Department (BLS) of the Trial Court, Civil No. 03-05810-BLS (Justice van Gestel).

Affidavit of Richard Bijjani in Opposition to Plaintiff's Patent motions, in a case entitled *L-3 Communications Security and Detection Systems Corporation Delaware v. Reveal Imaging Technologies, Inc.*, Commonwealth of Massachusetts, Superior Court Department (BLS) of the Trial Court, Civil No. 03-05810-BLS (Justice van Gestel).

Affidavit of A. W. Phinney in Opposition to Plaintiff's Emergency Motion Regarding "Newly Found Evidence", Redacted Version, in a case entitled *L-3 Communications Security and Detection Systems Corporation Delaware v. Reveal Imaging Technologies, Inc.*, Commonwealth of Massachusetts, Superior Court Department (BLS) of the Trial Court, Civil No. 03-05810-BLS (Justice van Gestel).
Affidavit of Elan Scheinman in Opposition to Plaintiff's Patent Motions, Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).
Affidavit of A. W. Phinney in Opposition to Plaintiff's Patent Motions, Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).
Affidavit of Michael Ellenbogen in Opposition to Plaintiff's Emergency Motion, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).
Affidavit of Michael Ellenbogen in Opposition to Plaintiff's Patent Motions, Redacted Version, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).
Plaintiff's Amended Verified Complaint dated May 18, 2004 in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS1 (Justice van Gestel).
Defendant's Answer dated May 24, 2004 in a case entitled *L-3 Communications Security and Detection Systems Corporation Delaware* v. *Reveal Imaging Technologies, Inc.* Commonwealth of Massachusetts, Superior Court Department (BLS) of the Trial Court, Civil No. 03-05810-BLS1 (Justice van Gestel).
The Court's "Memorandum and Orders on Various Motions and Related Matters" dated Dec. 2, 2004, in a case entitled *L-3 Communications Security and Detection Systems Corporation Delaware* v. *Reveal Imaging Technologies, Inc.*, Commonwealth of Massachusetts, Superior Court Department (BLS) of the Trail Court, Civil No. 03-05810-BLS1 (Justice van Gestel).
Decision On Petition in *In re* Ellenbogen, et al.
International Search Report for PCT/US2003/31718, mailed Jun. 11, 2004.
International Search Report for PCT/US2004/001929, mailed Jul. 14, 2004.
Eilbert and Krug, "Aspects of Image Recognition in Vivid Technology's Dual-energy X-ray System for Explosive Detection," Proceedings of the International Society for Optical Engineering, vol. 1824, Nov. 1992.
Decision on Petition, in Re: Ellenbogen et al., Apr. 22, 2005.
The Reveal Parties' Supplemental Answers to Plaintiff's Second Set of Interrogatories, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS (Justice van Gestel).
Exhibits 6-8 from the Reveal Parties Memorandum in Support of Their Motion for Summary Judgment Concerning Plaintiff's Purported Trade Secrets #1 and #2, dated Aug. 2, 2005, in a case entitled *L-3 Communications Security and Detection Systems Corporation Delaware* v. *Reveal Imaging Technologies, Inc.*, Commonwealth of Massachusetts, Superior Court Department (BLS) of the Trial Court, Civil No. 03-05810-BLS1 (Justice van Gestel).
Second Affidavit of Norbert J. Pelc dated Aug. 25, 2005, in a case entitled *L-3 Communications Security and Detection Systems Corporation Delaware* v. *Reveal Imaging Technologies, Inc.*, Commonwealth of Massachusetts, Superior Court Dept. of the Trial Court, Civil Action No. 03-5810-BLS (Judge van Gestel).
McStay, Marshall, E-mail entitled, "Argus Grant Proposal," dated Jul. 11, 2002, with Attachment entitled, "Deployment.prop.doc," (pp. 97 through 1-97-4).
Scheinman, PowerPoint Presentation entitled, "Developing Checked Baggage Inspection Systems," dated Apr. 29, 2002, pp. 1,2, 15-18 (pp. 98-1 through 98-6).
Luetkemeier, Michael, E-mail entitled, "DCA Pic," with Attachment "Lobby.jpg," dated May 2, 2002, (pp. 103-1 through 103-2), printed Jul. 13, 2006.
Scheinman, Elan, E-mail, entitled, "Draft E:Mail to TSA," dated Mar. 15, 2002, (p. 104-1).
Presentation printed from a file entitled, "Final Slides Check Baggage Systems 042902 2.ppt," (pp. 105-1 through 105-4).
Scheinman, Elan, E-Mail dated Feb. 25, 2002, entitled, "[Fwd:Layouts]," with Attachment entitled, "Layouts," (pp. 106-1 through 106-11).
Scheinman, Elan, E-mail entitled, "JAX write-up," with Attachment entitled, "Jacksonville HBS Layout2.doc," dated May 29, 2002, (pp. 108-1 through 108-9).
"Vivid Check-In Desk Explosives Detection System Technical Proposal," printed Jul. 13, 2006, (pp. 110-1 through 110-45).
Scheinman, Elan, E-mail entitled, "Passenger and Baggage Screening," with Attachment entitled, "Jacksonville HBS layout 2.doc," dated Feb. 15, 2002, (pp. 111-1 through 111-9).
Scheinman, Elan, E-mail, entitled, "Pict. from TRW," with Attachment entitled, "Lobby CT pict.jpg," dated May 2, 2002, (pp. 112-1 throrugh 112-2).
Scheinman, Elan, E-mail entitled, "Re: (no subject)," dated Apr. 19, 2002, (p. 114-1).
Scheinman, Elan, E-mail entitled, "Re: DCA Pic," dated May 2, 2002, printed Jul. 13, 2006, (p. 115-1).
Scheinman, Elan, E-mail dated Feb. 13, 2002, entitled, "Re: [Fwd: JAX]," (p. 116-1).
Miller, Norm, E-mail dated Jun. 18, 2002, entitled, "Re: SW-JAX," (p. 117-1).
Miller, Norm, E-mail entitled, "SW-JAX," with Attachment entitled, "SW Alternate EDS.doc," dated Jun. 19, 2002, (pp. 118-11 through 18-2).
Scheinman, Elan, E-mail dated Feb. 4, 2002, entitled, "Write-Up for JAX," with Attachment entitled, "Jacksonville HBS layout.doc," (pp. 119-1-119-6).
PerkinElmer Instruments, "Check-In Desk X-ray Screening System "Bronze" Technical Proposal Jeddah International Airport," dated May 2000, (pp. 120-1 through 120-31).
Ellenbogen, Michael, E-mail entitled, "Jeddah," dated Jul. 28, 1999, (p. 121-1).
Scheinman, Elan, E-mail entitled, "[Fwd: Two Alternatives, L3 Machines in Portland Jetway]," with Attachment entitled, "Two Alternatives, L3 Machines in Portland Jetway," dated Aug. 16, 2002, (pp. 122-1 through 122-4).

\* cited by examiner

COMPUTED TOMOGRAPHY SYSTEM

RELATED APPLICATIONS

This application is a continuation-in-part of U.S. patent application Ser. No. 10/677,976, entitled "Folded Array CT Baggage Scanner" and filed on Oct. 2, 2003.

FIELD OF THE INVENTION

The present invention is directed to the field of computed tomography detection systems.

BACKGROUND OF INVENTION

On Nov. 16, 2001, the U.S. Congress passed the Aviation and Transportation Security Act. The Act required U.S. airlines to perform 100% checked baggage inspection starting Jan. 18, 2002 using any means available, with a requirement to inspect 100% of the checked bags using FAA Certified Explosives Detection Systems (EDS) by Dec. 31, 2002. Accordingly, a system that enables the airlines and airports to comply with those regulations while maintaining passenger and baggage flow through the terminal is needed.

The currently available EDS technology can be deployed in the terminal in front of the check-in counter, creating a new passenger queue and significant logistical problems for the airlines, or they can be integrated into the baggage conveyor system behind the check-in counters.

There are currently two deployment options for computed tomography (CT) machines; free standing or integrated. In a freestanding mode, the CT is installed in the airport lobby. Passengers are required to queue for checked baggage inspection prior to queuing for check-in. Freestanding installations consume a great deal of real estate in the airport terminal and require the user to make extensive modifications to existing passenger processing protocols.

Integrated installations are actually built into the conveyor system after check-in. Whether built into the conveyor just aft of the check-in desks or further down the baggage handling system, these installations are very expensive and require extensive modifications to the baggage conveyor system.

In view of the foregoing, a need exists for an operational friendly and usable screening system.

SUMMARY OF THE INVENTION

An embodiment of the invention is directed to a computed tomography device, comprising a tunnel to receive baggage, an x-ray source providing an x-ray beam that intersects the tunnel and has a beam angle of 120°, a gantry that oscillates relative to the tunnel through an oscillation angle that equals 270°, and a plurality of detectors. The plurality of detectors are mounted to the gantry and adapted to receive x-rays from the x-ray source. In addition, the plurality of detectors are arranged in a horseshoe-shaped configuration in which at least one first detector is located a furthest distance from the x-ray source and at least one second detector is disposed on each side of the at least one first detector and is disposed closer to the x-ray source than the at least one first detector.

DETAILED DESCRIPTION

One embodiment of the invention is directed to a smaller and cheaper system than is provided by traditional detection systems, and which is designed to be integrated into a check-in desk. Installing the inspection system within the check-in desk addresses critical drawbacks associated with existing equipment.

Standard check-in time is consistent with the screening time needed by the CT system. Screening at the check-in desk keeps the passenger with his bag until the bag is cleared, thereby avoiding the need to re-unite the passenger and bag at another point. A check-in desk solution does not require the complete baggage handling system to track 100% of all bags, which would require most US airports to update their baggage handling systems (BHS) at significant expense.

The check-in desk system may replace the existing check-in desk. Space requirements may be 15–20% greater than the existing check-in counters. The check-in desk system may be both freestanding and integrated. Because it is freestanding, it consumes none of the existing real estate in the terminal, eliminates the need for additional screening queues in front of the check-in process, and minimizes the need for a significant number of operators and screeners. Because it is integrated, it eliminates the need to replace the existing baggage conveyor system, significantly reduces cost, and allows quick installation of the screening system, rather than a year or more of planning.

The check-in desk system uses Computed Tomography (CT) which involves taking different X-ray projections from many different angles around an object and then performing a series of computations to reconstruct all pixels within an object. CT uses a rotating X-ray source to create "slice" images. CT was the first procedure that let physicians look inside the brain without opening the skull. The same principle holds true for security. CT allows you to see a small object like a sheet of plastic explosive, hidden inside the thick metal walls of a radio or laptop much like CT allows you to see a small tumor hidden behind the skull bone.

Computed Tomography is a proven automated explosives detection technique. FAA certification has been achieved using CT technology.

Most CTs have a rotating gantry holding the X-ray source and detectors, performing continuous 360° rotations. CT systems designed for baggage inspection rotate at speeds between 30 and 120 RPM. Rotating large, heavy components at these speeds significantly complicates the system design. From slip rings and bearings to high speed radio frequency data transmission systems, each element of the machine is designed to support the 360° rotation.

One embodiment of the invention is directed to a very simple, slow CT machine. The CT rotates only 270° and then rotates back. Because the system uses an oscillating, rather than rotating design, the design of each element becomes much more simple and straightforward. The machine may be designed from mostly off-the shelf components, thereby making it easy and inexpensive to develop a production capability.

Figure 1:
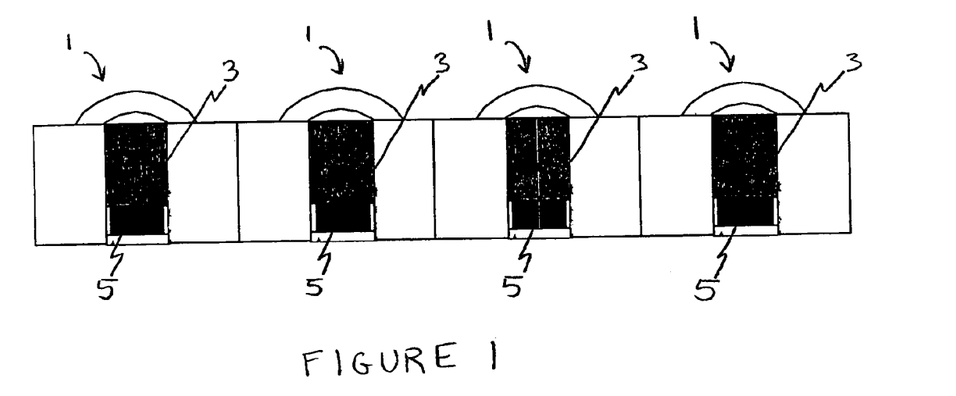
FIG. 1 illustrates a line of check-in counters with integrated CT scanners according to one embodiment of the invention.
Figure 2:
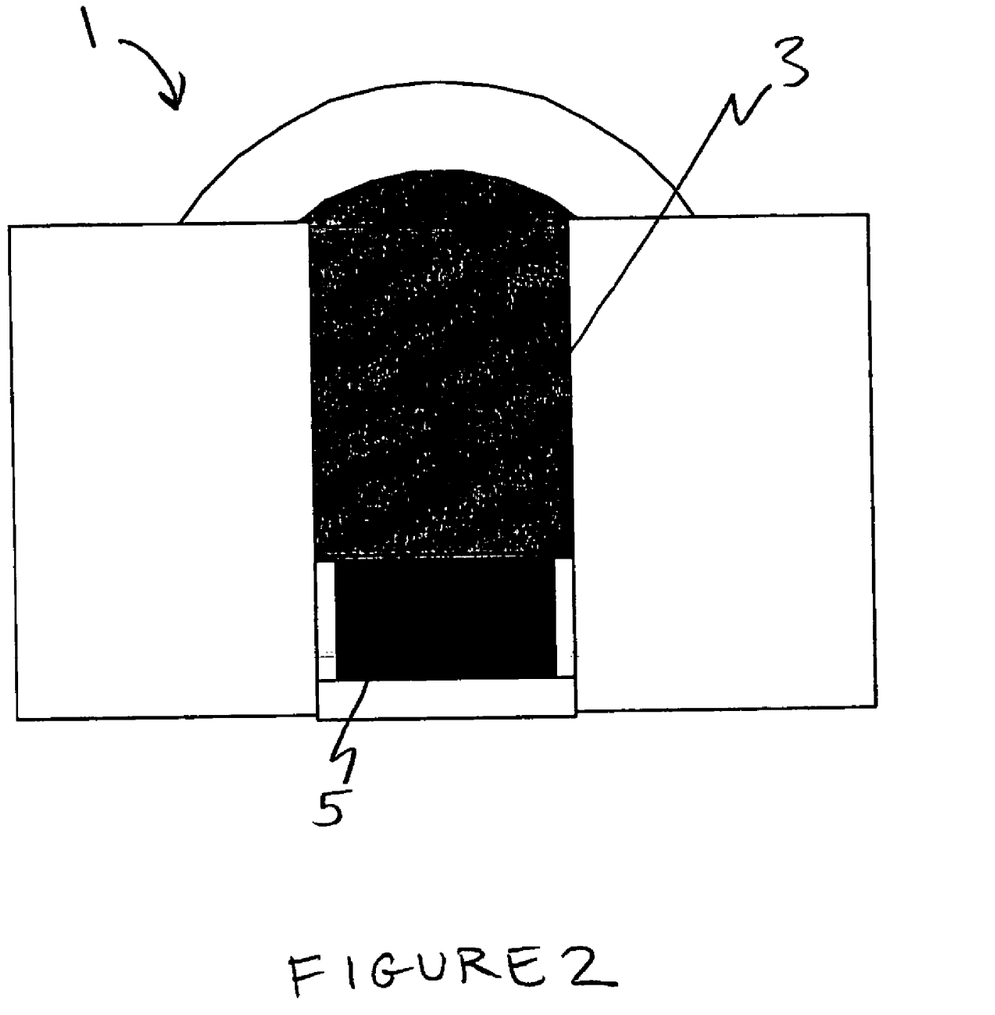
FIG. 2 illustrates an enlarged view of a single one of the integrated CT scanners of FIG. 1.
Figure 3:
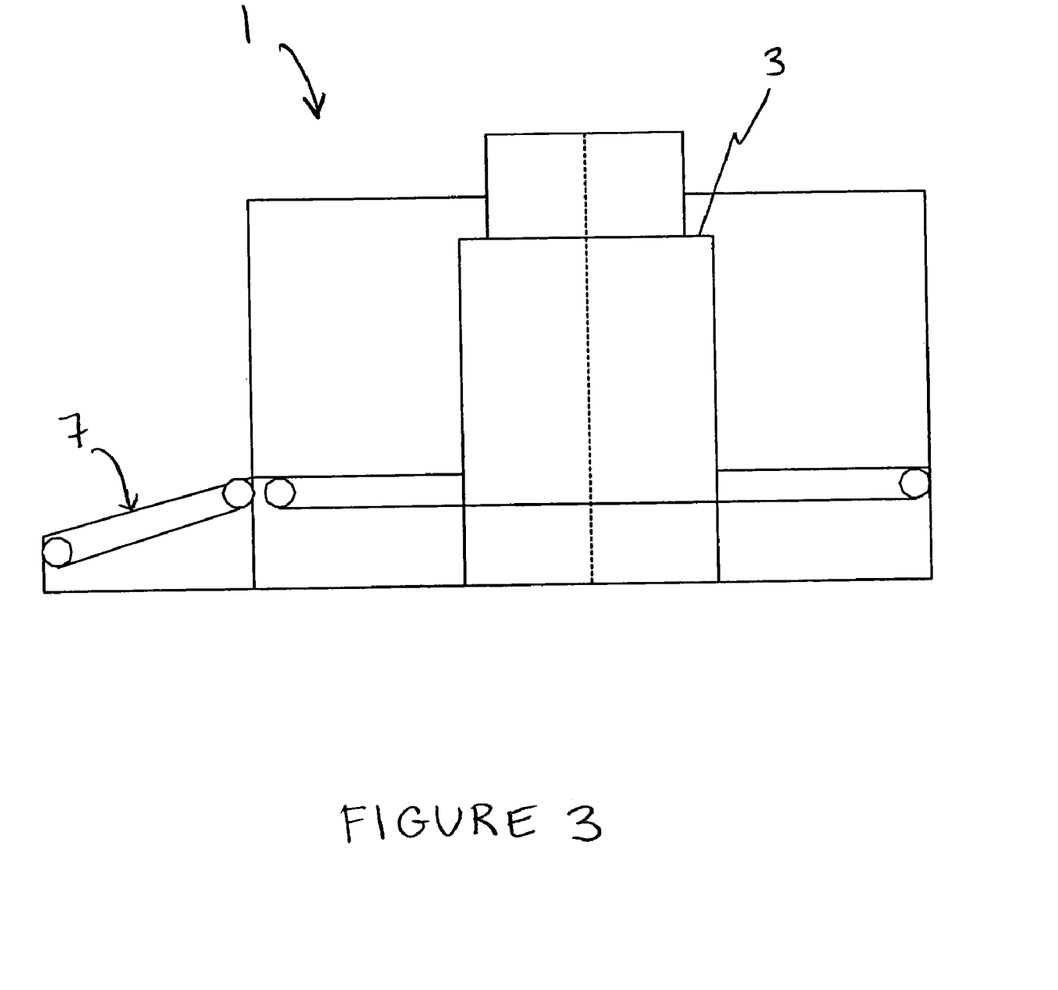
FIG. 3 illustrates a side view of the integrated CT scanner of FIG. 2.

A unique combination of off-the-shelf technologies may be configured in the smallest possible package designed to be integrated into a standard sized check-in desk. FIG. 1 illustrates a line of check-in counters 1 with integrated CT scanners 3 according to one embodiment of the invention. Openings 5 are provided for the loading of baggage. FIG. 2 illustrates an enlarged view of one of the integrated CT scanners 3. FIG. 3 illustrates a side view of the CT scanner of FIG. 2. A conveyor 7 carries baggage loaded through opening 5 (FIG. 2) through the CT scanner 3.

Figure 4:
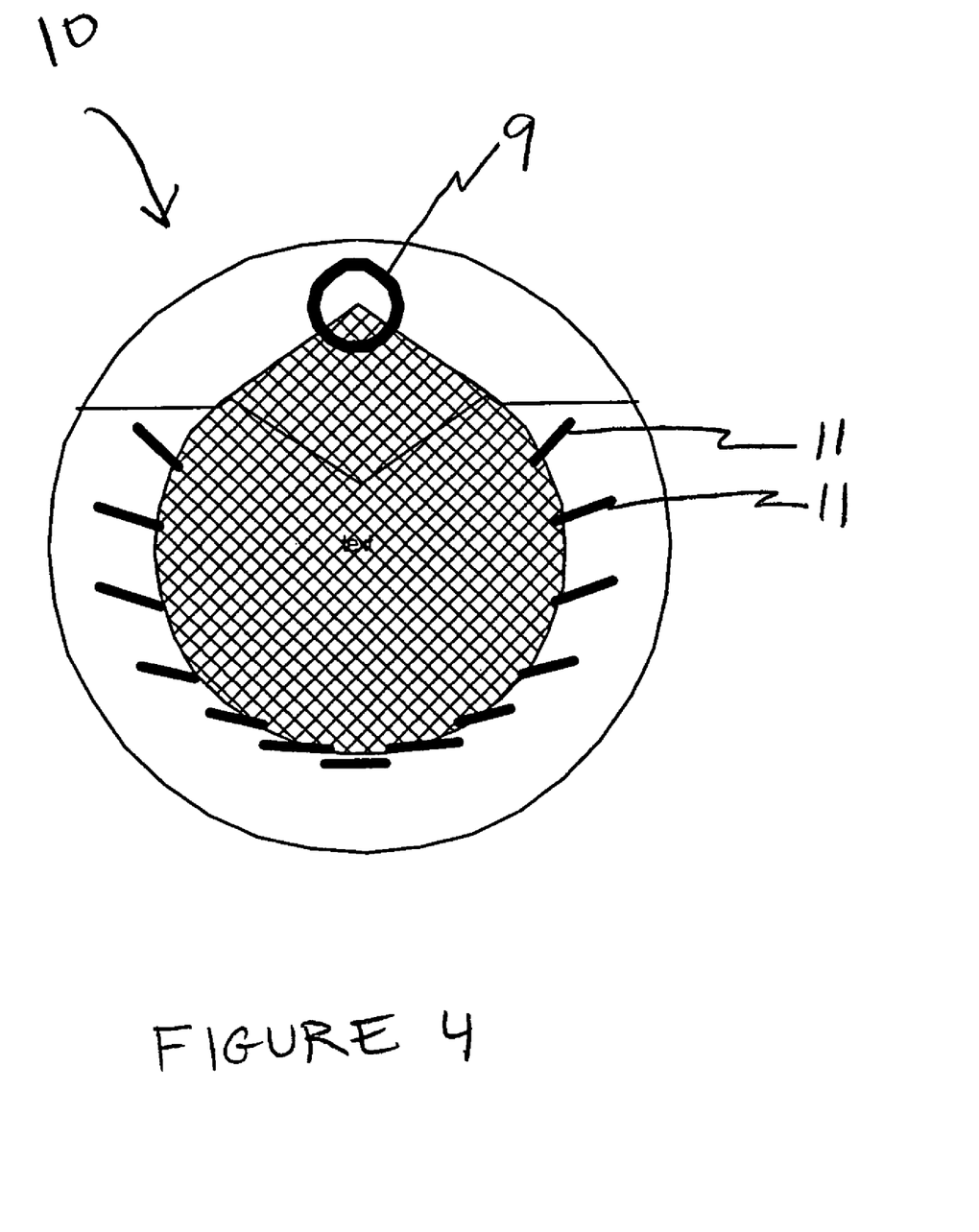
FIG. 4 illustrates an arrangement of an x-ray source and detectors in a CT system according to one embodiment of the invention.

Industry average processing times at the check-in area are one passenger every 2.5 minutes. Because the CT scanner is built into the check-in desk in accordance with one embodiment, bags may be inspected as passengers are checking in. Thus, a complete bag scan can take up to one minute. Scanning slowly allows the X-ray source to oscillate, rather than requiring a complete rotation for each "slice". Since a complete 360° rotation is not required, the CT scanner does not require a slip ring, which comprises the most complex parts of a conventional CT system, and is used to transfer power and data to the rotating X-ray gantry. Instead, in one embodiment the design uses an oscillating "horseshoe" architecture. FIG. 4 illustrates the oscillating horseshoe architecture according to an embodiment of the invention, in which a x-ray source 9 is oriented to direct x-rays towards detectors 11.

When computed tomography is performed without a complete 360° rotation, a number of technical issues become significantly easier to address. A first group of issues relate to the power supply. Traditional slip-ring CTs require the X-ray source and power supply be mounted to the gantry. Rather than mounting the X-ray source and high voltage power supplies on the rotating gantry, these components can be mounted in the chassis of the system, thereby simplifying the system design and minimizing technical risk.

Another group of issues relate to the Data Acquisition System (DAS). Traditional slip-ring CTs require that the data acquisition system be mounted to the gantry, with a means, typically a radio frequency (RF) transmitter, to transfer data to a CPU located in the chassis of the machine. In one embodiment, rather than mounting the DAS and associated components to the gantry, these components can be mounted in the chassis of the system, thereby simplifying the system design, reducing cost and minimizing technical risk.

A further group of issues relate to system size. Mounting all of the system electronics, including a complete power supply and X-ray source, quickly expands the size of the gantry itself. By mounting many of these components in the chassis of the machine, the gantry can be minimized, which provides a significant advantage when placing a CT inside a check-in desk sized envelope, as it facilitates minimizing the size of the system's external envelope.

Figures 5A, 5B:
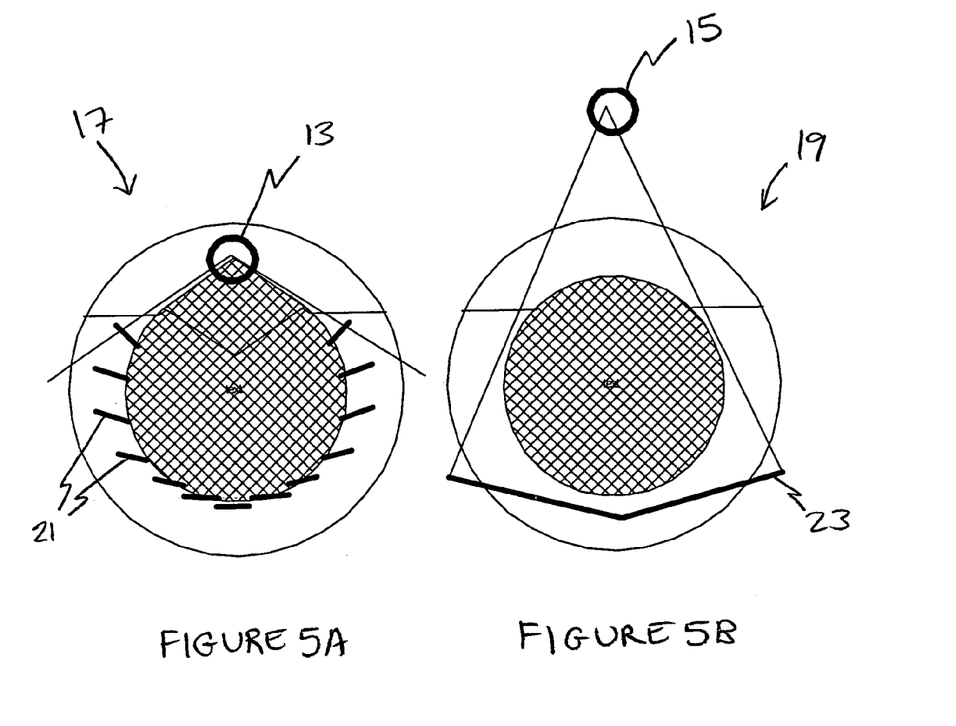
FIG. 5A illustrates an arrangement of an x-ray source and detectors in a CT system employing a wide angle x-ray source according to one embodiment of the invention.
FIG. 5B illustrates the arrangement of the x-ray source and detectors in a traditional CT system

The size of the CT gantry depends on the size of the circle of reconstruction and the X-ray source angle. Most CTs use an X-ray source with between 60° and 80° angle. The "horseshoe" system architecture, because so few components reside on the rotating device, allows the use of a commercial off-the-shelf X-ray source. X-ray sources from commercial non-destructive testing market are available with up to 180° beam angle. As the beam angle gets wider, the total size of the CT shrinks. This is illustrated in FIGS. 5A–B. FIG. 5A illustrates a CT system 17 with a 120° X-ray source 13 oriented to direct x-rays towards detectors 21 according to an embodiment of the invention. FIG. 5B illustrates a traditional CT system 19 with 60° X-ray source 15 oriented to direct x-rays towards detectors 23.

Having thus described some illustrative embodiments of the invention, various modifications and improvements will readily occur to those skilled in the art. Accordingly, the foregoing description is by way of example only and is not intended as limiting. The invention is limited only as defined in the following claims and the equivalents thereto.

What is claimed is:

1. A computed tomography device, comprising:
   a tunnel to receive baggage;
   an x-ray source providing an x-ray beam that intersects the tunnel and has a beam angle of 120°;
   a gantry that oscillates relative to the tunnel through a rotation angle that equals at least 270° and is less than 360°; and
   a plurality of detectors mounted to the gantry and adapted to receive x-rays from the x-ray source, the plurality of detectors being arranged in a horseshoe-shaped configuration in which at least one first detector is located a furthest distance from the x-ray source, and at least one second detector is disposed on each side of the at least one first detector and is disposed closer to the x-ray source than the at least one first detector.

2. A computed tomography system, comprising:
   a tunnel to receive at least one object;
   a wide-angle x-ray source providing an x-ray beam that intersects the tunnel and has a beam angle of greater than 80°;
   a gantry that is movable relative to the tunnel; and
   a plurality of detectors mounted to the gantry and adapted to receive x-rays from the x-ray source.

3. The computed tomography system of claim 2, wherein the at least one object is at least one item of baggage.

4. The computed tomography system of claim 2, wherein the x-ray beam has a beam angle of approximately 120°.

5. The computed tomography system of claim 2, wherein the x-ray beam has a beam angle between 120° and 180°.

6. The computed tomography system of claim 2, wherein the plurality of detectors are mounted to the gantry in a horse-shoe shaped configuration.

7. The computed tomography system of claim 2, wherein the gantry is movable relative to the tunnel through a rotation angle that is less than 360°.

8. The computed tomography system of claim 2, wherein the gantry is movable relative to the tunnel in an oscillating motion.

9. The computed tomography system of claim 8, wherein the gantry is movable relative to the tunnel in an oscillating motion back and forth through a rotation angle less than 360° between a first position relative to the tunnel and a second position relative to the tunnel.

10. The computed tomography system of claim 2, wherein the system does not include a slip ring coupled to the gantry.

11. The computed tomography system of claim 2, wherein the gantry moves relative to the tunnel at a speed such that a time to complete a scan of the at least one object is approximately one minute.

12. The computed tomography system of claim 2, wherein the x-ray source is mounted on the gantry.

13. The computed tomography system of claim 2, further comprising:

a chassis; and a data acquisition system that is mounted on the chassis and coupled to the plurality of detectors.

14. The computed tomography system of claim 2, wherein the x-ray source is mounted adjacent the tunnel.

15. The computed tomography system of claim 2, wherein the x-ray source is mounted immediately adjacent the tunnel.

16. The computed tomography system of claim 2, in combination with a check-in desk area, wherein the tunnel passes through the check-in desk area.

17. The computed tomography system of claim 16, wherein the check-in desk area has a front side and a back side, and wherein the tunnel comprises a first opening on the front side of the check in area and a second opening on the back side of the check-in area.

18. The computed tomography system of claim 16, wherein the check-in desk area comprises a plurality of adjacent check-in desks.

19. The computed tomography system of claim 2, wherein the plurality of detectors comprises first and second detectors mounted to the gantry such that the first detector is disposed a first distance from the x-ray source and the second detector is disposed a second distance from the x-ray source, wherein the first and second distances are different.

20. The computed tomography system of claim 19, wherein the plurality of detectors further comprises a third detector mounted to the gantry such that the third detector is disposed a third distance from the x-ray source, wherein the first and third distances are the same, and wherein each of the first and third distances is shorter than the second distance.

21. The computed tomography system of claim 2, wherein the plurality of detectors comprises first and second detectors mounted to the gantry such that a first angle is formed between the first detector and a first tangent of the tunnel that is nearest the first detector, and a second angle is formed between the second detector and a second tangent of the tunnel that is nearest the second detector, wherein the first and second angles are different.

22. The computed tomography system of claim 21, wherein the first and second detectors are mounted to the gantry such that the first detector is disposed a first distance from the x-ray source and the second detector is disposed a second distance from the x-ray source, wherein the first and second distances are different.

23. The computed tomography system of claim 2, wherein an axis passes through a center of the gantry and bisects the gantry into first and second halves, and wherein at least a first one of the plurality of detectors is disposed on the first half of the gantry and at least a second one of the plurality of detector is disposed on the second half of the gantry.

24. The computed tomography system of claim 2, wherein at least some of the plurality of detectors are mounted to the gantry so as to receive x-rays from outer portions of the x-ray beam.

25. A computed tomography device, comprising:

a tunnel to receive at least one object;

an x-ray source providing an x-ray beam that intersects the tunnel;

a gantry that is movable relative to the tunnel, the gantry having an opening therethrough; and a detector array comprising a plurality of disjoint segments disposed around the opening, the detector array comprising a plurality of detectors mounted to the gantry and adapted to receive x-rays from the x-ray source, the plurality of detectors comprising at least first and second detectors mounted to the gantry in a first of the disjoint segments and a second of the disjoint segments, respectively, such that the first detector is disposed a first distance from the x-ray source and the second detector is disposed a second distance from the x-ray source, wherein the first and second distances are different.

26. The computed tomography device of claim 25, wherein the plurality of detectors further comprises third and fourth detectors mounted to the gantry such that the third detector is disposed a third distance from the x-ray source and the fourth detector is disposed a fourth distance from the x-ray source, wherein the first and third distances are the same and the second and fourth distances are the same.

27. The computed tomography device of claim 25, wherein the first detectors and second detectors are mounted at different angles with respect to the tunnel.

28. The computed tomography system of claim 25, wherein the at least one object is at least one item of baggage.

29. The computed tomography system of claim 25, wherein the x-ray beam has a beam angle of greater than 80°.

30. The computed tomography system of claim 25, wherein the x-ray beam has a beam angle of approximately 120°.

31. The computed tomography system of claim 25, wherein the x-ray beam has a beam angle between 120° and 180°.

32. The computed tomography system of claim 25, wherein the plurality of detectors are mounted in a horseshoe shaped configuration.

33. The computed tomography system of claim 25, wherein the gantry is movable relative to the tunnel through a rotation angle that is less than 360°.

34. The computed tomography system of claim 25, wherein the gantry is movable relative to the tunnel in an oscillating motion.

35. The computed tomography system of claim 34, wherein the gantry is movable relative to the tunnel in an oscillating motion back and forth through a rotation angle less than 360° between a first position relative to the tunnel and a second position relative to the tunnel.

36. The computed tomography system of claim 25, wherein the system does not include a slip ring coupled to the gantry.

37. The computed tomography system of claim 25, wherein the gantry moves relative to the tunnel at a speed such that a time to complete a scan of the at least one object is approximately one minute.

38. The computed tomography system of claim 25, wherein the x-ray source is mounted on the gantry.

39. The computed tomography system of claim 25, further comprising:

a chassis; and a data acquisition system that is mounted on the chassis and coupled to the plurality of detectors.

40. The computed tomography system of claim 25, wherein the x-ray source is mounted adjacent the tunnel.

41. The computed tomography system of claim 25, wherein the x-ray source is mounted immediately adjacent the tunnel.

42. The computed tomography system of claim 25, in combination with a check-in desk area, wherein the tunnel passes through the check-in desk area.

43. The computed tomography system of claim 42, wherein the check-in desk area has a front side and a back side, and wherein the tunnel comprises a first opening on the front side of the check in area and a second opening on the back side of the check-in area.

44. The computed tomography system of claim 42, wherein the check-in desk area comprises a plurality of adjacent check-in desks.

45. The computed tomography system of claim 25, wherein the plurality of detectors comprises first and second detectors mounted to the gantry such that the first detector is disposed a first distance from the x-ray source and the second detector is disposed a second distance from the x-ray source, wherein the first and second distances are different.

46. The computed tomography system of claim 45, wherein the plurality of detectors further comprises a third detector mounted to the gantry such that the third detector is disposed a third distance from the x-ray source, and wherein the first and third distances are the same, and wherein each of the first and third distances is shorter than the second distance.

47. The computed tomography system of claim 25, wherein the plurality of detectors comprises first and second detectors mounted to the gantry such that a first angle is formed between the first detector and a first tangent of the tunnel that is nearest the first detector, and a second angle is formed between the second detector and a second tangent of the tunnel that is nearest the second detector, wherein the first and second angles are different.

48. The computed tomography system of claim 47, wherein the first and second detectors are mounted to the gantry such that the first detector is disposed a first distance from the x-ray source and the second detector is disposed a second distance from the x-ray source, wherein the first and second distances are different.

49. The computed tomography system of claim 25, wherein an axis passes through a center of the gantry and bisects the gantry into first and second halves, and wherein at least a first detector of the plurality of detectors is disposed on the first half of the gantry and at least a second detector of the plurality of detector is disposed on the second half of the gantry.

50. The computed tomography system of claim 25, wherein at least some of the plurality of detectors are mounted to the gantry so as to receive x-rays from outer portions of the x-ray beam.

51. A computed tomography system, comprising:
an envelope having a sufficiently small size to allow it to be integrated into an airline check-in desk;
an x-ray source disposed within the envelope; and
a plurality of detectors disposed within the envelope and adapted to receive x-rays from the x-ray source.

52. An assembly, comprising:
at least one passenger check-in counter; and
an x-ray screening system at least partially integrated within the at least one check-in counter.

53. The assembly of claim 52, wherein the x-ray screening system is a computed tomography system.

54. The assembly of claim 53, wherein:
the at least one check-in counter comprises first and second check-in counters adjacent to each other;
the computed tomography system is a first computed tomography system and is at least partially integrated within the first check-in counter; and
the assembly further comprises a second computed tomography system at least partially integrated within the second check-in counter.

55. The assembly of claim 54, wherein:
the first and second check-in counters are located between the first computed tomography system and the second computed tomography system.

56. The assembly of claim 53, wherein:
the at least one check-in counter comprises first and second check-in counters, and
the computed tomography system is located between the first and second check-in counters.

57. The assembly of claim 53, wherein:
the at least one check-in counter comprises a plurality of check-in counters; and
the assembly further comprises a plurality of computed tomography systems that include the computed tomography system, wherein a number of the check-in counters is equal to twice a number of the computed tomography systems.

58. The assembly of claim 53, further comprising a tunnel that passes through the at least one check-in counter and the computed tomography system.

59. The assembly of claim 53, wherein the computed tomography system, comprises:
a tunnel to receive at least one object;
a wide-angle x-ray source providing an x-ray beam that intersects the tunnel and has a beam angle of greater than 80°;
a gantry that is movable relative to the tunnel; and
a plurality of detectors mounted to the gantry and adapted to receive x-rays from the x-ray source.

60. The assembly system of claim 59, wherein the plurality of detectors comprises first and second detectors mounted to the gantry such that the first detector is disposed a first distance from the x-ray source and the second detector is disposed a second distance from the x-ray source, wherein the first and second distances are different.

61. The assembly system of claim 59, wherein the plurality of detectors comprises first and second detectors mounted to the gantry such that a first angle is formed between the first detector and a first tangent of the tunnel that is nearest the first detector, and a second angle is formed between the second detector and a second tangent of the tunnel that is nearest the second detector, wherein the first and second angles are different.

62. The assembly of claim 53, wherein the computed tomography system, comprises:
a tunnel to receive at least one object;
an x-ray source providing an x-ray beam that intersects the tunnel;
a gantry that is movable relative to the tunnel; and
a plurality of detectors mounted to the gantry and adapted to receive x-rays from the x-ray source, the plurality of detectors comprising at least first and second detectors mounted to the gantry such that the first detector is disposed a first distance from the x-ray source and the second detector is disposed a second distance from the x-ray source, wherein the first and second distances are different.

63. The assembly system of claim 62, wherein the plurality of detectors comprises first and second detectors mounted to the gantry such that a first angle is formed between the first detector and a first tangent of the tunnel that is nearest the first detector, and a second angle is formed between the second detector and a second tangent of the tunnel that is nearest the second detector, wherein the first and second angles are different.

64. The assembly system of claim 62, wherein the x-ray source is a wide-angle x-ray source providing an x-ray beam having a beam angle of greater than 80°.

65. A method of processing an airline passenger, comprising acts of:
checking in an airline passenger at a check-in desk; and
while checking in the airline passenger, simultaneously scanning an item of luggage of the passenger at the check-in desk using an x-ray screening system.

66. The method of claim 65, wherein the act of simultaneously scanning the item of luggage comprises simultaneously scanning the item of luggage of the passenger at the check-in desk using a computed tomography system.

67. The method of claim 66, further comprising an act of:
transporting the item of luggage from a first side of the check-in desk to a second side of the check-in desk by moving the item of baggage through the computed tomography system.

68. The method of claim 65, wherein the item of luggage is checked luggage.

69. The method of claim 65, wherein the act of simultaneously scanning the item of luggage is completed before the act of checking in the airline passenger is complete.

70. The method of claim 65, wherein the act of scanning takes approximately one minute to complete.

71. The method of claim 65, wherein the computed tomography system comprises an x-ray source and detectors, and wherein the act of scanning comprises imaging a slice of the item of baggage by oscillating the detectors of the computed tomography system through an oscillation angle less than 360°.

72. A computed tomography system, comprising:
a tunnel to receive at least one object;
a gantry that is movable relative to the tunnel;
a wide-angle x-ray source mounted to the gantry and providing an x-ray beam that intersects the tunnel and has a beam angle greater than 80°; and
a plurality of detectors mounted to the gantry and adapted to receive x-rays from the x-ray source, wherein the plurality of detectors comprises first, second and third detectors mounted to the gantry such that the first detector is disposed a first distance from the x-ray source, the second detector is disposed a second distance from the x-ray source, and the third detector is disposed a third distance from the x-ray source, wherein the first and second distances are different, wherein the first and third distances are the same, and wherein each of the first and third distances is shorter than the second distance.

73. The computed tomography system of claim 72, in combination with a check-in desk area, wherein the tunnel passes through the check-in desk area.

74. The computed tomography system of claim 72, wherein the plurality of detectors comprises first and second detectors mounted to the gantry such that a first angle is formed between the first detector and a first tangent of the tunnel that is nearest the first detector, and a second angle is formed between the second detector and a second tangent of the tunnel that is nearest the second detector, wherein the first and second angles are different.

75. The computed tomography system of claim 72, wherein an axis passes through a center of the gantry and bisects the gantry into first and second halves, and wherein at least a first one of the plurality of detectors is disposed on the first half of the gantry and at least a second one of the plurality of detector is disposed on the second half of the gantry.

76. A method of selecting components for use in producing a computed tomography (CT) system, comprising an act of:

(A) selecting a wide-angle x-ray source having a beam angle of greater than 80° so that an external envelope of the CT system can be minimized.

77. The method of claim 76, wherein the act (A) comprises selecting a wide-angle x-ray source having a beam angle of approximately 120°.

78. The method of claim 76, wherein the act (A) comprises selecting a wide-angle x-ray source having a beam angle between 120° and 180°.

79. The method of claim 76, further comprising an act of:
(B) selecting a plurality of detectors arranged to receive x-rays from the x-ray source, the plurality of detectors comprising first and second detectors arranged such that the first detector is disposed a first distance from the x-ray source and the second detector is disposed a second distance from the x-ray source, wherein the first and second distances are different.

80. The method of claim 79, wherein the act (B) comprises an act of selecting a plurality of detectors that further comprises a third detector arranged such that the third detector is disposed a third distance from the x-ray source, wherein the first and third distances are the same, wherein each of the first and third distances is shorter than the second distance, and wherein the first and third detectors are disposed on opposite sides of the second detector.

81. An assembly of detectors for use in a computed tomography (CT) system comprising an x-ray source, the assembly of detectors comprising:
a detector array comprising a plurality of disjoint segments disposed around a periphery of an opening in the assembly, the detector array comprising a plurality of detectors adapted to receive x-rays from the x-ray source, the plurality of detectors comprising at least first and second detectors arranged so that the x-rays travel a first distance from the x-ray source to the first detector and the x-rays travel a second distance from the x-ray source to the second detector, wherein the first and second distances are different and the first detector is in a first of the disjoint segments and the second detector is in a second of the disjoint segments.

82. The assembly of claim 81, wherein the plurality of detectors further comprises a third detector arranged so that the x-rays travel a third distance from the x-ray source to the third detector, wherein the first and third distances are the same, wherein each of the first and third distances is shorter than the second distance, and wherein the first and third detectors are disposed on opposite sides of the second detector.

83. The assembly of claim 81, wherein the plurality of detectors are arranged in a horse-shoe shaped configuration.

84. The assembly of claim 81, in combination with a gantry moveably mounted in the CT system, wherein the plurality of detectors are mounted to the gantry.

85. The combination of claim 84, further in combination with the x-ray source, wherein the x-ray source is mounted to the gantry and has a beam angle of greater than 80°.

86. The combination of claim 84, wherein the x-ray beam has a beam angle of approximately 120°.

87. The combination of claim 84, wherein the x-ray beam has a beam angle between 120° and 180°.

88. The assembly of claim 84, wherein an axis passes through a center of the gantry and bisects the gantry into first and second halves, wherein at least a first detector of the plurality of detectors is disposed on the first half of the gantry and at least a second detector of the plurality of detectors is disposed on the second half of the gantry.

* * * * *